(12) United States Patent
Chinomi

(10) Patent No.: US 11,151,760 B2
(45) Date of Patent: Oct. 19, 2021

(54) IMAGE RECONSTRUCTION PROCESSING METHOD, IMAGE RECONSTRUCTION PROCESSING PROGRAM, AND TOMOGRAPHY DEVICE EQUIPPED WITH SAME

(71) Applicant: Shimadzu Corporation, Kyoto (JP)

(72) Inventor: Kenta Chinomi, Kyoto (JP)

(73) Assignee: Shimadzu Corporation, Kyoto (JP)

( * ) Notice: Subject to any disclaimer, the term of this patent is extended or adjusted under 35 U.S.C. 154(b) by 645 days.

(21) Appl. No.: 15/932,305

(22) PCT Filed: Aug. 17, 2015

(86) PCT No.: PCT/JP2015/073057
§ 371 (c)(1),
(2) Date: Feb. 16, 2018

(87) PCT Pub. No.: WO2017/029702
PCT Pub. Date: Feb. 23, 2017

(65) Prior Publication Data
US 2020/0286265 A1 Sep. 10, 2020

(51) Int. Cl.
*G06T 11/00* (2006.01)
*G06T 5/40* (2006.01)

(52) U.S. Cl.
CPC .............. *G06T 11/008* (2013.01); *G06T 5/40* (2013.01); *G06T 11/006* (2013.01); *G06T 2207/10081* (2013.01)

(58) Field of Classification Search
CPC ... G06T 2211/424; G06T 11/008; G06T 5/40; G06T 11/006; G06T 2207/10081;
(Continued)

(56) References Cited

U.S. PATENT DOCUMENTS 6,426,988 B2 * 7/2002 Yamada ................ G06T 11/005
378/4
8,175,361 B2 5/2012 Kunze et al.
(Continued)

FOREIGN PATENT DOCUMENTS

JP 2011-156302 A 8/2011
JP 2011-203160 A 10/2011
WO 2015/092588 A2 6/2015

OTHER PUBLICATIONS

Bilger, K., et al. "Threshold calculation for segmented attenuation correction in PET with histogram fitting." IEEE Transactions on nuclear science 48.1 (2001): 43-50. (Year: 2001).*
(Continued)

*Primary Examiner* — Siamak Harandi
(74) *Attorney, Agent, or Firm* — Maier & Maier, PLLC

(57) ABSTRACT

The image reconstruction processing method estimates, in a substance information estimation process, substance information from a reconstructed image for every image update in an image update process, and uses the estimated substance information to update images based on succeeding calculations by successive approximation formulae of a successive approximation method. Since the substance information is estimated, the present methodology can be applied regardless of whether the constituent substance of an imaging sample is known. Further, because the substance information is estimated (updated) from the reconstructed image for every image update in the image update process, reliable substance information can be estimated by avoiding the problem of continuously using the substance information estimated at a point of time where a repeat count (iteration count) by successive approximation formulae is low and at
(Continued)

a point of time where the repeat count is high. Accordingly, artifacts can be reduced using the reliable substance information.

8 Claims, 9 Drawing Sheets

(58) Field of Classification Search
CPC .... G16H 50/30; A61B 6/5205; A61B 6/5217; A61B 6/032; A61B 6/03
See application file for complete search history.

(56) References Cited

U.S. PATENT DOCUMENTS

| | | | | |
|---|---|---|---|---|
| 2013/0156163 A1* | 6/2013 | Liu | ....................... | G06T 11/005 378/207 |
| 2014/0002737 A1* | 1/2014 | Damberg | ................. | H04N 9/64 348/488 |
| 2015/0190106 A1* | 7/2015 | Yamakawa | .......... | A61B 6/5205 378/4 |
| 2015/0305702 A1* | 10/2015 | Sakimoto | ............. | A61B 6/5258 382/131 |
| 2016/0321803 A1* | 11/2016 | Lamash | ............... | A61B 6/5205 |

OTHER PUBLICATIONS

Search Report dated Jun. 29, 2018 in corresponding European Application No. 15901684.9; 7 pages.
Japanese Office Action dated Jan. 29, 2019, in connection with corresponding JP Application No. 2017-535173 (7 pgs., including machine-generated English translation).
International Search Report dated Nov. 10, 2015 of corresponding International application No. PCT/JP2015/073057; 6 pgs.
C. Lemmens et al., "Suppression of Metal Artifacts in CT Using a Reconstruction Procedure That Combines MAP and Projection Completion", IEEE Transactions on Medical Imaging, vol. 28 Issue:2(2009); 12 pgs.

* cited by examiner

[FIG. 1]
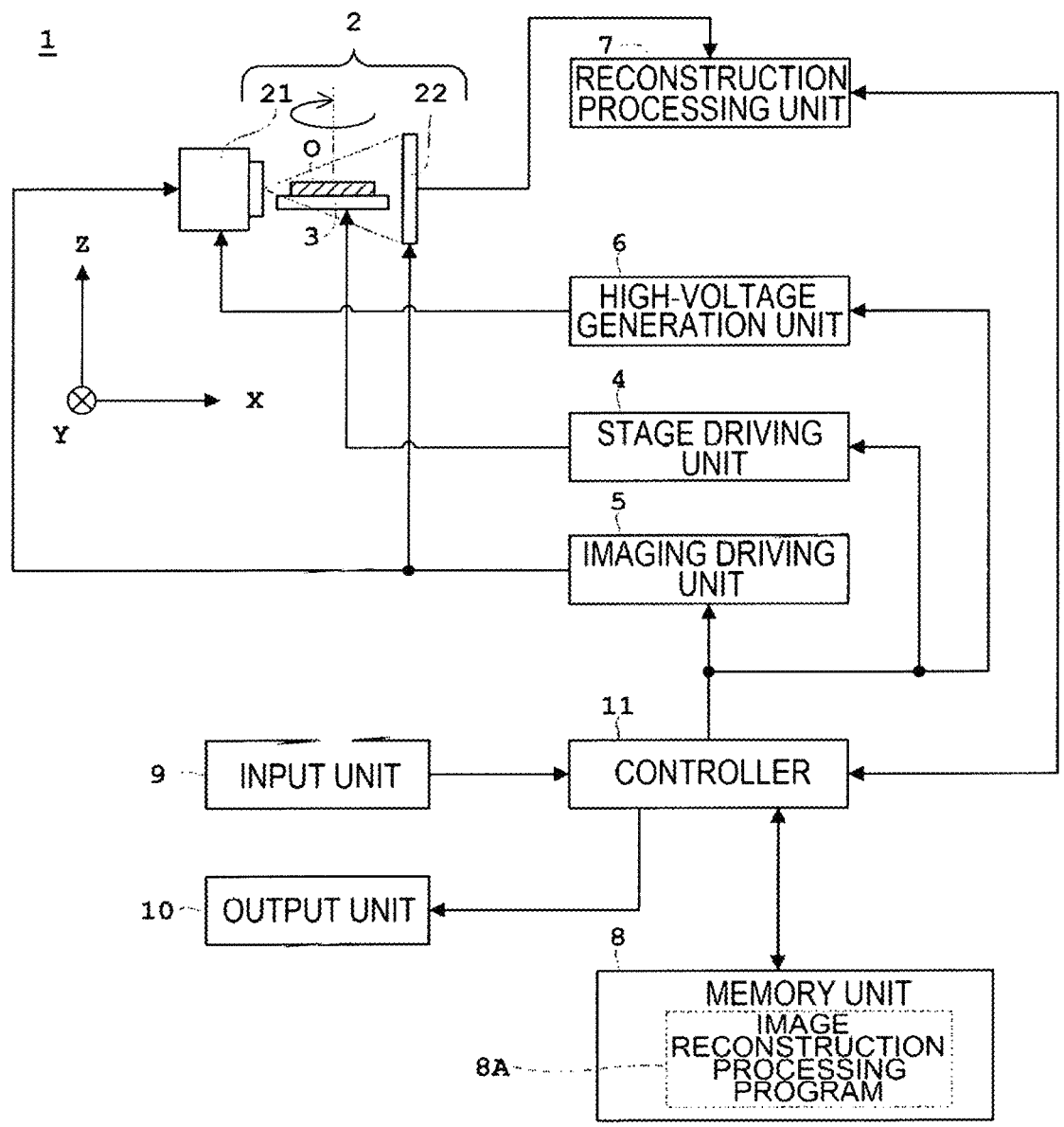

[FIG. 2]
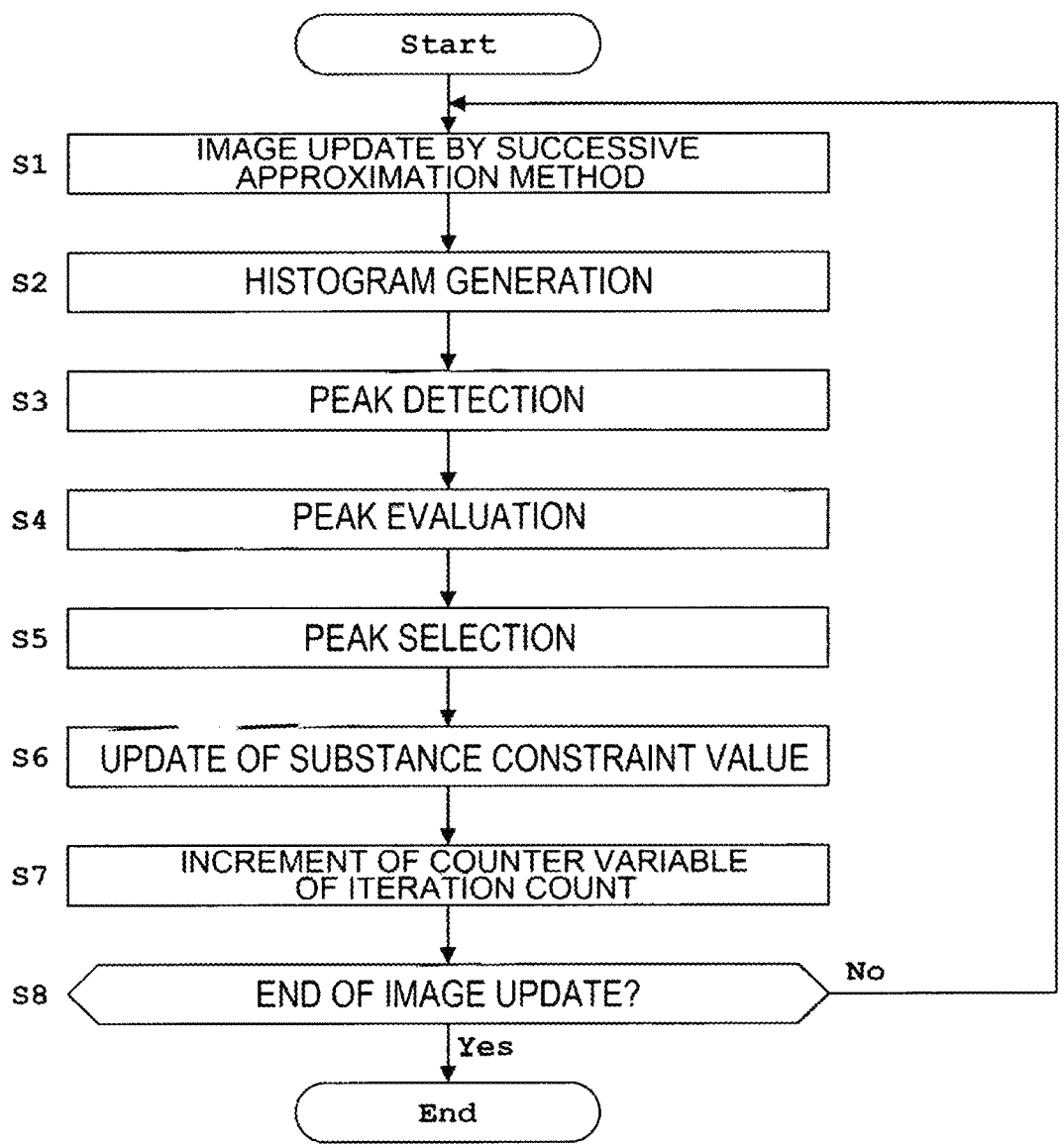

[FIG. 3]
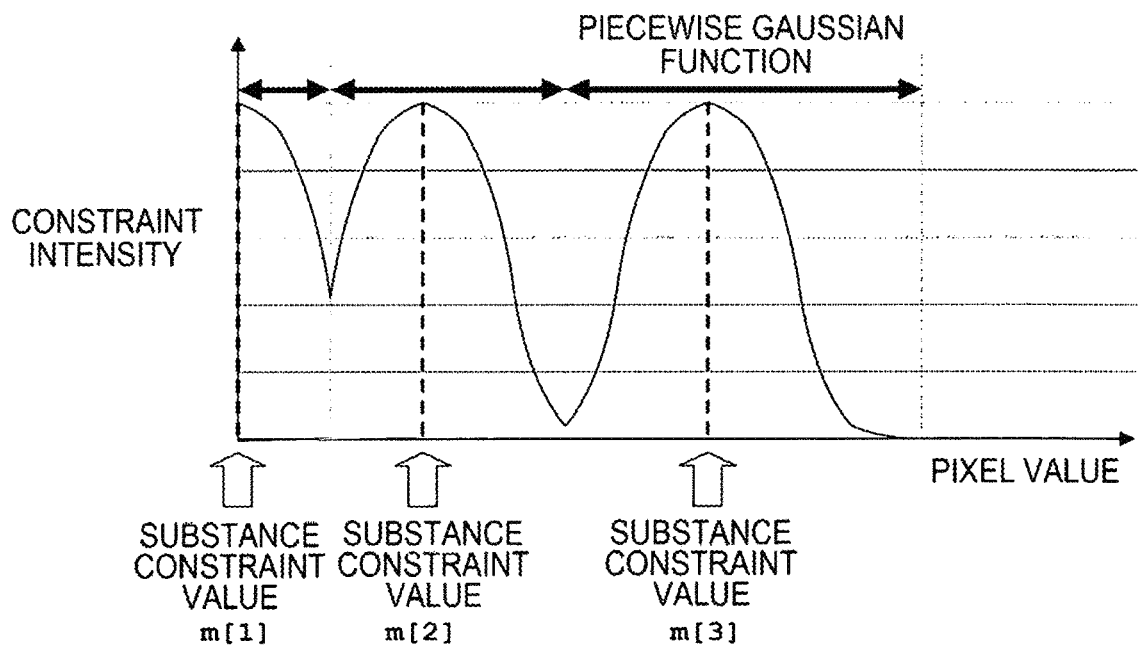
[FIG. 4]
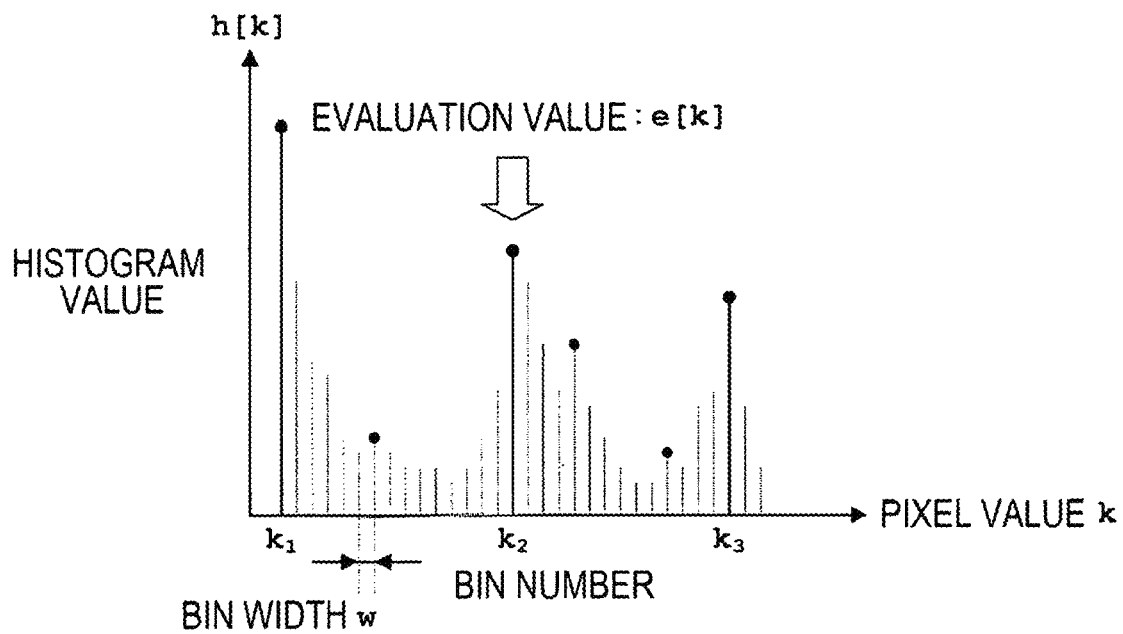

[FIG. 5]
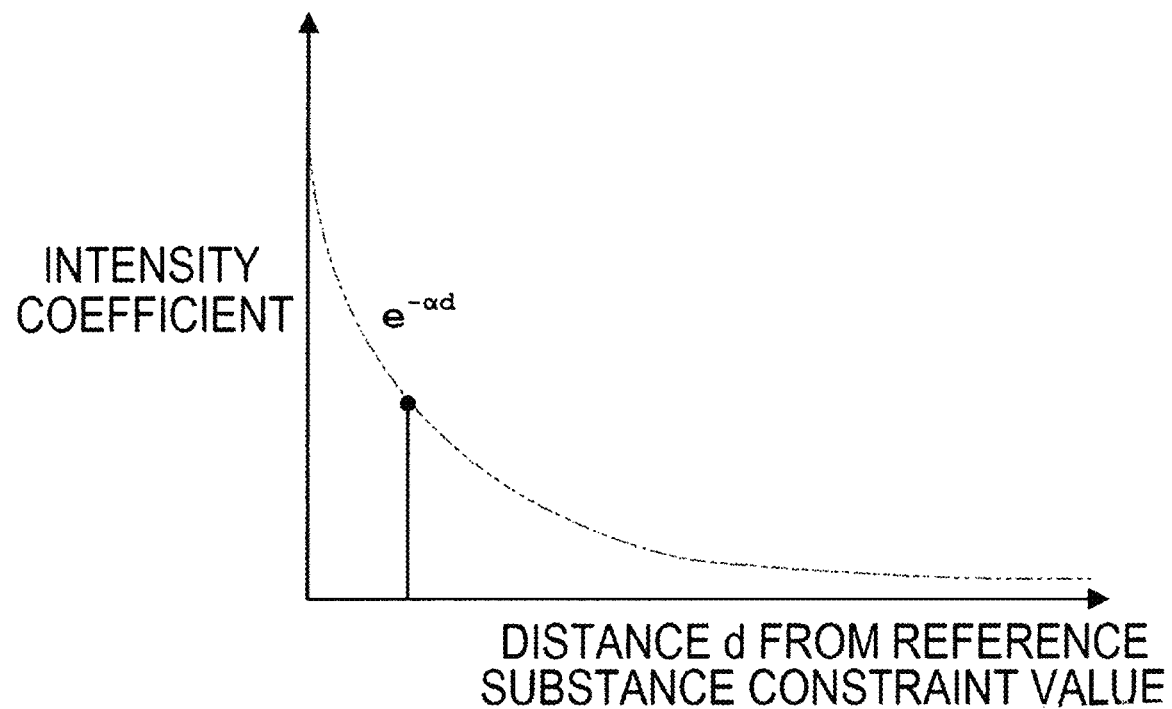

[FIG. 6]
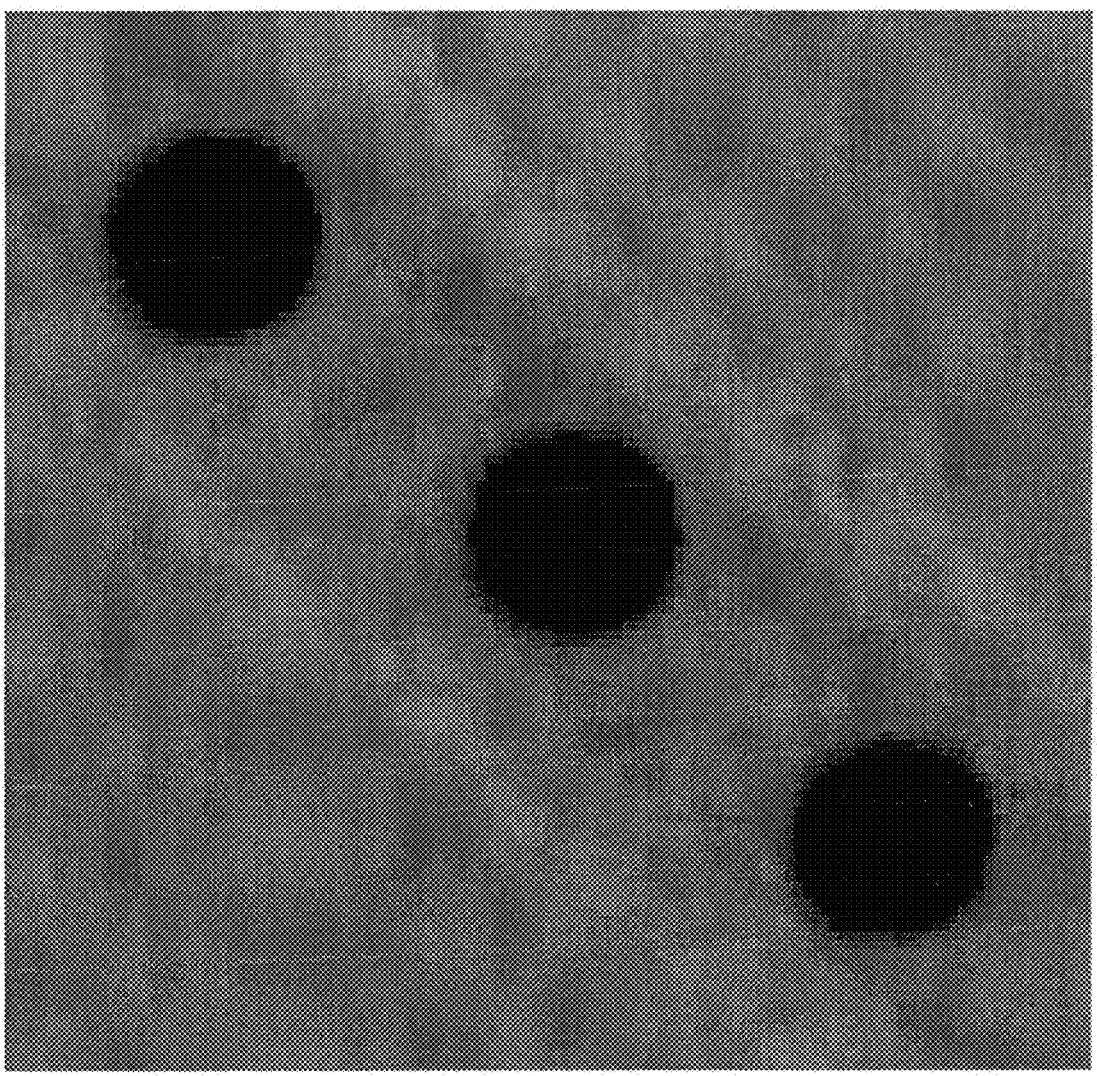

[FIG. 7]
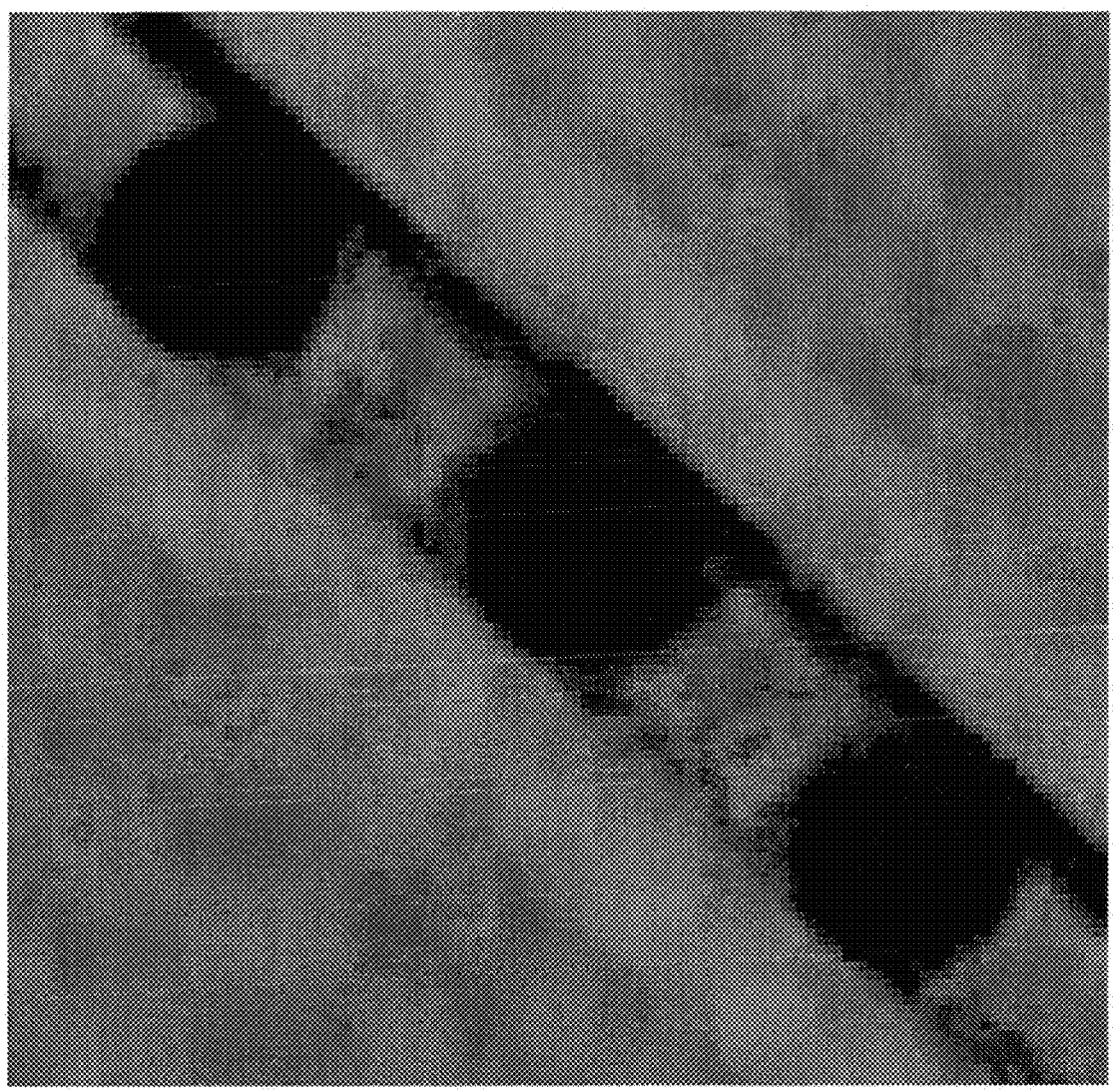

[FIG. 8]
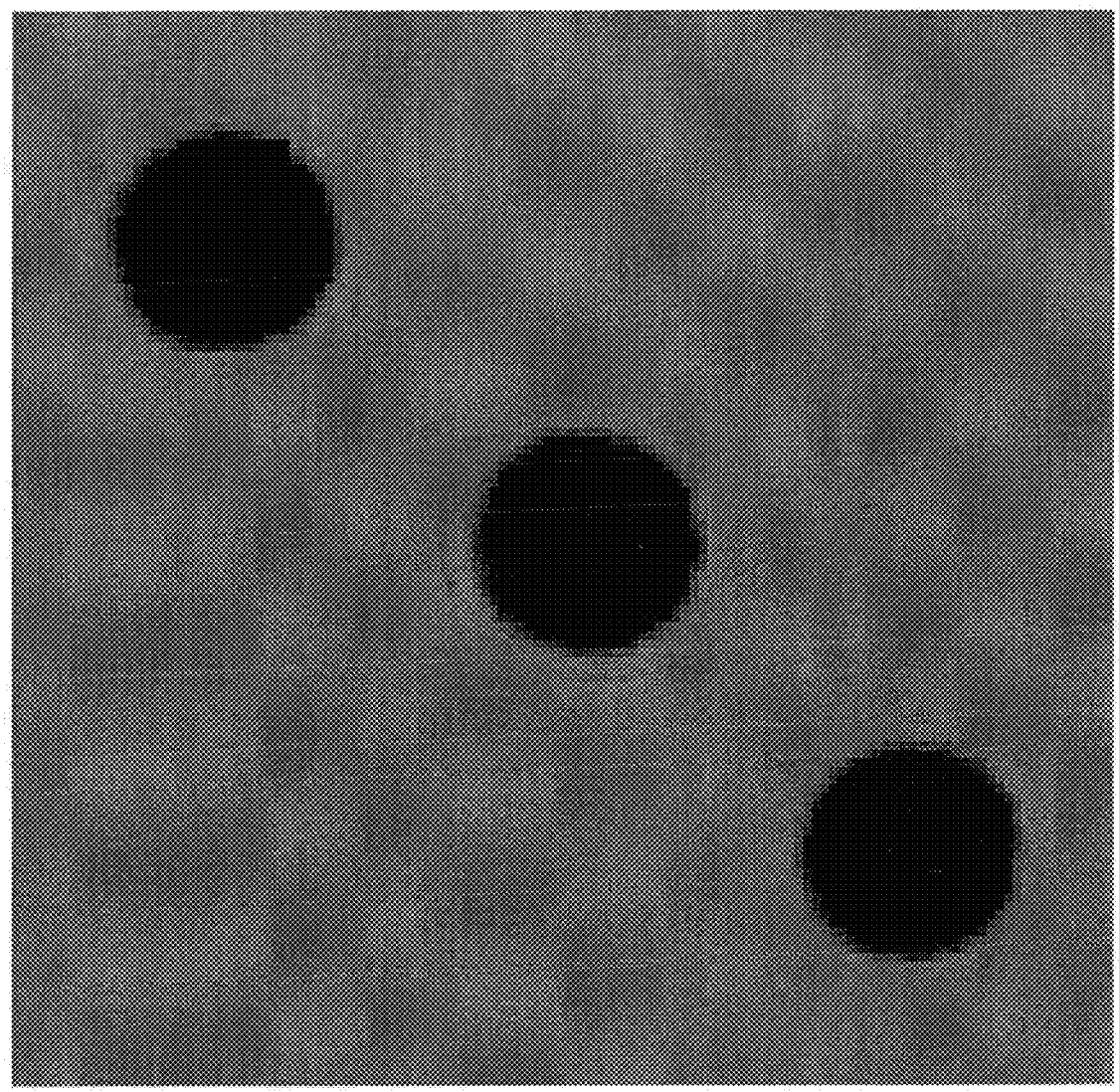

[FIG. 9]
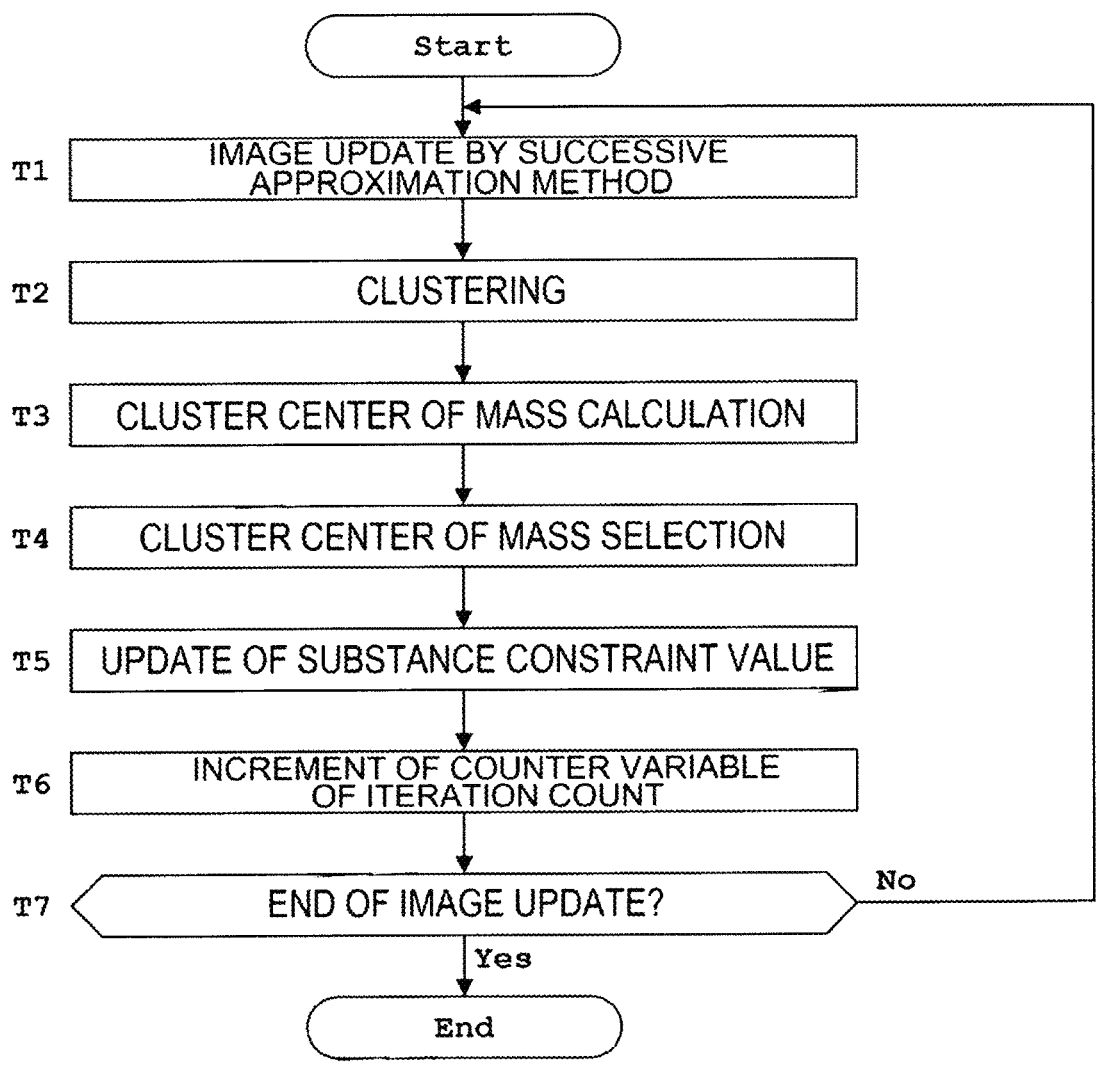

[FIG. 10]
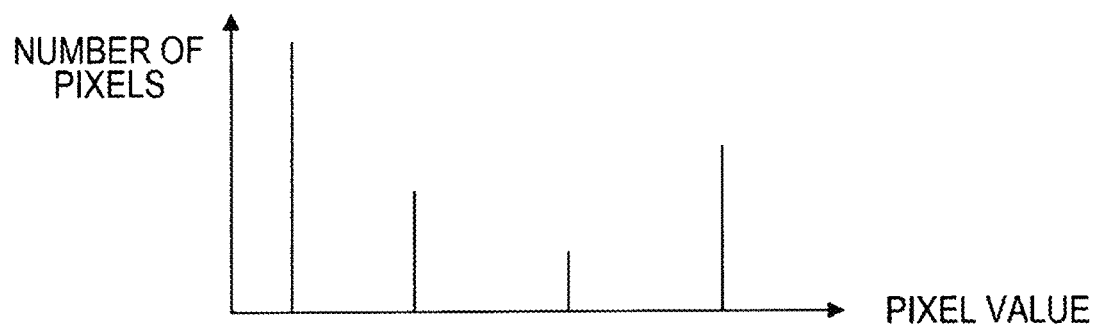
[FIG. 11]
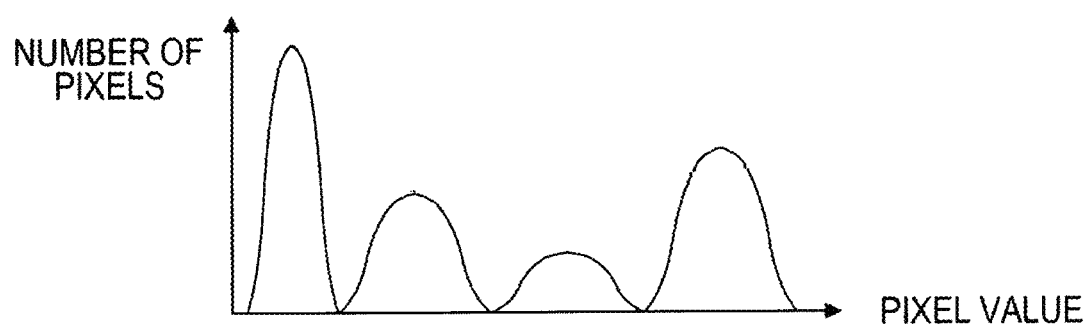
[FIG. 12]
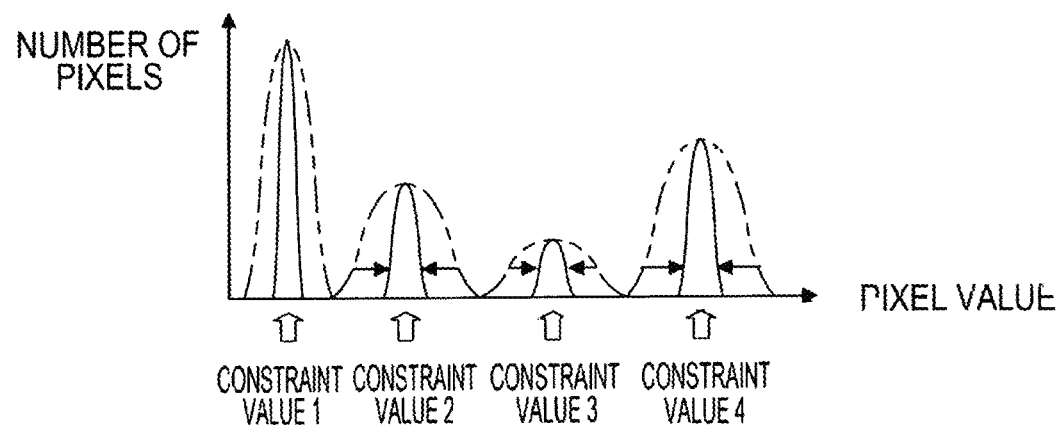

IMAGE RECONSTRUCTION PROCESSING METHOD, IMAGE RECONSTRUCTION PROCESSING PROGRAM, AND TOMOGRAPHY DEVICE EQUIPPED WITH SAME

FIELD

The present invention relates to a technique for reducing reconstruction artifacts caused by a successive approximation method in an image reconstruction processing method, an image reconstruction processing program, and a tomography device equipped with the same.

BACKGROUND

A tomography device is described with an X-ray computed tomography (CT) device taken as an example. Heretofore, a filtered back projection method (FBP) has been used as a standard image reconstruction method in X-ray CT. In recent years, in combination with an increase in performance of computing machinery, the study and practical use of image reconstruction using a successive approximation method have been progressing. While, in X-ray CT, the occurrence of artifacts caused by various factors is a longstanding problem, the successive approximation method is characterized by being capable of reflecting, for example, a complex physics model or prior information (previous knowledge) so as to reduce artifacts, and, heretofore, various techniques have been proposed (for example, see Patent Literatures 1 and 2 and Non-Patent Literature 1).

Of these, the techniques which are proposed in Patent Literature 2: JP-A-2011-156302 and Non-Patent Literature 1 use a "maximum a posteriori probability" (MAP) estimation that is based on Bayes' theorem, and give information concerning constituent substances of an imaging sample (substance information) as a prior probability, thus aiming at obtaining a better solution. In other words, those techniques are approaches to give such an effect that a reconstructed pixel has a pixel value of the previously-designated substance (the value representing an X-ray absorption coefficient), thus reducing artifacts.

Moreover, the technique which is proposed in Patent Literature 1: U.S. Pat. No. 8,175,361 provides regularization (constraint) using substance information in the successive approximation method and obtains the regularization term thereof from the histogram of an image. In other words, that technique is an approach to obtaining substance information based on the histogram of an image (see FIG. 4 in Patent Literature 1), and incorporating a regularization term using the substance information (see a regularization term R(X) in Patent Literature 1) into the second term of the right-hand side of a successive approximation formula (see formula (3) in Patent Literature 1), thus reducing artifacts.

The effect of this substance information is described in terms of an image histogram. Furthermore, the vertical axis of histograms illustrated in FIG. 10 to FIG. 12 used for description is expressed while being normalized with the maximum value of the number of pixels, and the horizontal axis of the histograms indicates a pixel value, which becomes higher as it comes closer to the right. As an example, consider an imaging sample which is configured with four types of materials having X-ray absorption coefficients different from each other. If an ideal condition in which, for example, the materials are pure substances and no noise occurs is assumed, as illustrated in FIG. 10, it appears that four peaks are present in the histogram of a reconstructed image.

However, actually, artifacts occur due to various factors, so that each peak in the histogram has a distribution with a width as illustrated in FIG. 11. On the other hand, substance information is given as pixel value sets (four substance constraint values) which the reconstructed image can take, and the center of each pixel value distribution would correspond to one substance constraint value. In response to the substance information functioning, pixel values present at the periphery of the distribution are pulled and gathered toward the center of the distribution as illustrated in FIG. 12. As a result, the pixel value distribution with a width becomes close to a precipitous peak, so that an ideal image, in other words, an image with artifacts reduced, can be obtained.

Patent Literature 1: U.S. Pat. No. 8,175,361
Patent Literature 2: JP-A-2011-156302
Non-Patent Literature 1: C. Lemmens: Suppression of Metal Artifacts in CT Using a Reconstruction Procedure That Combines MAP and Projection Completion, IEEE Transactions on Medical Imaging, Volume: 28 Issue: 2 (2009)

SUMMARY

However, in the conventional art proposed in Patent Literature 2: JP-A-2011-156302 and Non-Patent Literature 1, since it is necessary that constituent substances of an imaging sample are known, there is a problem in that the conventional art cannot be applied to an imaging sample the constituent substances of which are unknown. Moreover, in a case where the constituent substances are not pure substances (for example, in the case of an alloy), there is a problem in that X-ray absorption coefficients vary according to blend ratios. In this way, there is also a case where, even if the constituent substances are known, substance information to be given cannot be correctly recognized, so that the conventional art still cannot be applied.

On the other hand, in the conventional art proposed in Patent Literature 1: U.S. Pat. No. 8,175,361, substance information is estimated based on the histogram of an image, and, therefore, the conventional art can also be applied to an imaging sample the constituent substances of which are unknown. However, in an image reconstruction using the successive approximation method, an image is not yet sufficiently reconstructed (having many artifacts and being blurring) at a point of time when a repeat count (iteration count) is low. Therefore, the substance information estimated at that point of time is also not a reliable value.

The invention has been made in view of the above circumstances, and has an object to provide an image reconstruction processing method, an image reconstruction processing program, and a tomography device equipped with the same, each of which can be applied regardless of whether constituent substances of an imaging sample are known or unknown and each of which is capable of estimating reliable substance information, thus reducing artifacts using the reliable substance information.

The invention employs the following configuration so as to attain the above-mentioned object.

Specifically, an image reconstruction processing method of the invention, which is an image reconstruction processing method that performs reconstruction processing, is characterized by including an image update process of updating an image by a successive approximation method, and a substance information estimation process of estimating substance information from a reconstructed image for every image update in the image update process, at given intervals, at timing satisfying a given standard, or at optional timing, wherein the image reconstruction processing method performs reconstruction processing while updating an image by the successive approximation method in the image update process using the substance information estimated in the substance information estimation process.

According to the image reconstruction processing method of the invention, the substance information estimation process estimates substance information from a reconstructed image for every image update in the image update process, at given intervals, at timing satisfying a given standard, or at optional timing, and the image reconstruction processing method updates images in succeeding calculations by successive approximation formulae in the successive approximation method using the substance information estimated in the substance information estimation process. In this way, estimating substance information from a reconstructed image enables the invention to be applied regardless of whether constituent substances of an imaging sample are known or unknown. Moreover, while, in Patent Literature 1: U.S. Pat. No. 8,175,361, the estimated substance information is fixed, in the invention, substance information is estimated (updated) from a reconstructed image for every image update in the image update process, at given intervals, at timing satisfying a given standard, or at optional timing, so that reliable substance information can be estimated while avoiding such a problem that, for example, the substance information estimated at a point of time when a repeat count (iteration count) by successive approximation formulae is low is continuously used even at a point of time when the repeat count is high. Accordingly, artifacts can be reduced using the reliable substance information.

An example of the above-mentioned image reconstruction processing method of the invention is (a) estimating the substance information, which is to be estimated, based on the number of known constituent substances. Moreover, another example of the image reconstruction processing method is (b) estimating the substance information, which is to be estimated, based on the number of constituent substances given as a parameter. Additionally, yet another example of the image reconstruction processing method is (c) estimating the substance information, which is to be estimated, based on a substance constraint value given as a parameter.

In particular, in the case of (b) mentioned above, when the number of constituent substances is designated as a parameter regardless of the actual number of substances constituting an imaging sample, the substance information is estimated based on this parameter. In the case of (c) mentioned above, when a substance constraint value is given as a parameter regardless of whether constituent substances are known or unknown, the substance information is estimated based on this parameter. According to (a) mentioned above to (c) mentioned above, the possibility of erroneous substance information being estimated can be reduced or prevented. The substance information can be estimated by any one of (a) mentioned above to (c) mentioned above, or the substance information can be estimated by a combination of some of (a) mentioned above to (c) mentioned above. For example, the substance information can be estimated by a combination of (a) mentioned above and (c) mentioned above, or the substance information can be estimated by a combination of (b) mentioned above and (c) mentioned above.

In these above-mentioned image reconstruction processing methods of the invention, substance information, which is to be estimated, can be estimated based on a histogram of the reconstructed image, or substance information, which is to be estimated, can be estimated based on a result of clustering of the reconstructed image.

Moreover, an image reconstruction processing program of the invention is characterized by causing a computer to perform these image reconstruction processing methods of the invention.

According to the image reconstruction processing program of the invention, a computer is caused to perform these image reconstruction processing methods of the invention, so that the invention can be applied regardless of whether constituent substances of an imaging sample are known or unknown, reliable substance information can be estimated, and artifacts can be reduced using the reliable substance information.

Moreover, a tomography device of the invention, which is a tomography device equipped with an image reconstruction processing program of the invention, is characterized by including calculation means for executing the image reconstruction processing program.

According to the tomography device of the invention, calculation means for executing the image reconstruction processing program is included, so that the invention can be applied regardless of whether constituent substances of an imaging sample are known or unknown, reliable substance information can be estimated, and artifacts can be reduced using the reliable substance information.

According to the image reconstruction processing method related to the invention, substance information is estimated from a reconstructed image, so that the invention can be applied regardless of whether constituent substances of an imaging sample are known or unknown. Moreover, substance information is estimated (updated) from a reconstructed image for every image update in the image update process, at given intervals, at timing satisfying a given standard, or at optional timing, so that reliable substance information can be estimated while avoiding such a problem that, for example, the substance information estimated at a point of time when a repeat count (iteration count) by successive approximation formulae is low is continuously used even at a point of time when the repeat count is high. Accordingly, artifacts can be reduced using the reliable substance information.

Moreover, according to the image reconstruction processing program of the invention, a computer is caused to perform these image reconstruction processing methods of the invention, so that the invention can be applied regardless of whether constituent substances of an imaging sample are known or unknown, reliable substance information can be estimated, and artifacts can be reduced using the reliable substance information.

Moreover, According to the tomography device of the invention, calculation means for executing the image reconstruction processing program is included, so that the invention can be applied regardless of whether constituent substances of an imaging sample are known or unknown, reliable substance information can be estimated, and artifacts can be reduced using the reliable substance information.

BRIEF DESCRIPTION OF THE DRAWINGS

FIG. 1 is an outline diagram and a block diagram of a X-ray CT device according to an embodiment.

FIG. 2 is a flowchart of image reconstruction processing according to an embodiment.

FIG. 3 is a schematic diagram concerning a validity term of an objective function using a piecewise Gaussian function.

FIG. 4 is a schematic diagram provided for description of substance information estimation using a histogram.

FIG. 5 is a schematic diagram provided for description of an intensity coefficient $e^{-\alpha_i j}$.

FIG. 6 illustrates a reconstruction result obtained when no substance information is present.

FIG. 7 illustrates a reconstruction result obtained when substance information is not updated.

FIG. 8 illustrates a reconstruction result obtained when substance information has been updated.

FIG. 9 is a flowchart of image reconstruction processing according to a modification example.

FIG. 10 is a schematic diagram of an ideal histogram.

FIG. 11 is a schematic diagram of an actual histogram.

FIG. 12 is a schematic diagram of a histogram obtained by the effect of substance information.

DETAILED DESCRIPTION OF THE DRAWINGS

Hereinafter, embodiments of the invention will be described with reference to the drawings. FIG. 1 is an outline diagram and a block diagram of a X-ray CT device according to an embodiment. In the present embodiment, a tomography device is described with an X-ray CT device taken as an example.

As illustrated in FIG. 1, an X-ray CT device 1 according to the present embodiment includes an imaging unit 2, which captures an image of an object O, a stage 3, on which the object O is allowed to be placed, a stage driving unit 4, which drives the stage 3, an imaging driving unit 5, which drives the imaging unit 2, a high-voltage generation unit 6, which generates a high voltage to apply tube current or tube voltage to an X-ray tube 21 of the imaging unit 2, and a reconstruction processing unit 7, which performs reconstruction processing on projection data obtained by an X-ray detector 22 of the imaging unit 2. The reconstruction processing unit 7 is equivalent to calculation means in the invention.

The imaging unit 2 includes the X-ray tube 21, which irradiates the object O with X-rays, and the X-ray detector 22, which detects X-rays which have been radiated from the X-ray tube 21 and then have passed through the object O. Examples of the X-ray detector 22 include an image intensifier (I.I.) and a flat panel-type X-ray detector (flat panel detector (FPD)), but are not specifically limited. In the present embodiment, the X-ray detector 22 is described with a flat panel-type X-ray detector (FPD) taken as an example.

The FPD is configured with a plurality of detection elements arranged vertically and horizontally side by side in association with respective pixels, each detection element detecting X-rays, and outputs data about the detected X-rays (an electric charge signal) as an X-ray detection signal. In this way, the X-ray tube 21 radiates X-rays toward the object O, and the X-ray detector 22, which is configured with an FPD, detects X-rays to output an X-ray detection signal. Then, projection data is acquired by arranging, side by side, pixel values obtained based on the X-ray detection signal in association with respective pixels (detection elements).

The stage driving unit 4, which is configured with, for example, a motor and a drive shaft (both omitted from illustration), causes the stage 3 to rotate around a Z-axis center, illustrated in the figure, within a horizontal plane. According to the rotation of the stage 3 within a horizontal plane, the object O also rotates around the Z-axis center within a horizontal plane, so that a plurality of pieces of projection data is acquired.

As with the stage driving unit 4, the imaging driving unit 5 is configured with, for example, a motor and a drive shaft (both omitted from illustration). X-ray CT imaging is performed with the X-ray detector 22 and the X-ray tube 21 being moved in such a way as to face each other. Moreover, the magnification ratio in X-ray CT imaging can be changed by moving the X-ray tube 21 or the X-ray detector 22 in a horizontal direction (the X-direction illustrated in the figure). Moreover, image capturing can also be performed from an oblique direction relative to the object O with the X-ray tube 21 or the X-ray detector 22 slanted with respect to the X-axis.

The high-voltage generation unit 6 generates a high voltage to apply tube current or tube voltage to the X-ray tube 21, so that X-rays are generated from the X-ray tube 21 and the object O is irradiated with the generated X-rays. The reconstruction processing unit 7 acquires a reconstructed image concerning the object O by executing an image reconstruction processing program 8A described below. Specific functions of the reconstruction processing unit 7 are described below in detail.

Besides, the X-ray CT device 1 includes a memory unit 8, an input unit 9, an output unit 10, and a controller 11.

The memory unit 8 writes and stores therein data such as projection data obtained by the X-ray detector 22 and a reconstructed image obtained by the reconstruction processing unit 7, via the controller 11, and reads out the data as appropriate according to necessity to send projection data or a reconstructed image to the output unit 10 via the controller 11, thus outputting the data. The memory unit 0 is configured with a storage medium typified by, for example, a read-only memory (ROM) or a random-access memory (RAM).

In the present embodiment, a histogram of projection data or an updated reconstructed image (also called an "estimated image") is read out from the memory unit 8 and is then sent to the reconstruction processing unit 7 via the controller 11, so that image reconstruction processing (see the flowchart of FIG. 2), such as image update or substance information estimation, by the successive approximation method is performed. Moreover, the image reconstruction processing program 8A is previously stored in the memory unit 8, and the image reconstruction processing program 8A is read out from the memory unit 8 to the reconstruction processing unit 7 via the controller 11 and the reconstruction processing unit 7 then executes the image reconstruction processing program 8A, so that image reconstruction processing illustrated in the flowchart of FIG. 2 is performed. The image reconstruction processing program 8A is equivalent to an image reconstruction processing program in the invention.

The input unit 9 sends, to the controller 11, data or an instruction input by the operator. The input unit 9 is configured with a keyboard and a pointing device typified by, for example, a mouse, a joystick, a trackball, or a touch panel.

The output unit 10 is configured with, for example, a display unit typified by, for example, a monitor, or a printer. In the present embodiment, projection data or a reconstructed image is displayed on the monitor of the output unit 10.

The controller 11 comprehensively controls various portions configuring the X-ray CT device 1. Data such as projection data obtained by the X-ray detector 22 or a reconstructed image obtained by the reconstruction processing unit 7 is written and stored in the memory unit 8 or sent to the output unit 10, via the controller 11. In a case where the output unit 10 is a display unit, output displaying is performed, and, in a case where the output unit 10 is a printer, output printing is performed.

In the present embodiment, the reconstruction processing unit 7 or the controller 11 is configured with, for example, a central processing unit (CPU). Furthermore, the reconstruction processing unit 7 can also be configured with, for example, a graphics processing unit (GPU).

Next, specific functions of the reconstruction processing unit 7 (see FIG. 1) are described with reference to FIG. 2 to FIG. 5. FIG. 2 is a flowchart of image reconstruction processing according to an embodiment, FIG. 3 is a schematic diagram concerning a validity term of an objective function using a piecewise Gaussian function, FIG. 4 is a schematic diagram provided for description of substance information estimation using a histogram, and FIG. 5 is a schematic diagram provided for description of an intensity coefficient $e^{-\alpha_d}$.

(Step S1) Image Update by Successive Approximation Method

Images are updated by various types of successive approximation methods. Furthermore, it is desirable that processing for correcting physical characteristics (for example, beam hardening and diffusion) of the X-ray tube 21 (see FIG. 1) or the X-ray detector 22 (see FIG. 1) be included. While, in the present embodiment, such processing is preformed, in a case where these characteristics are negligible, that processing does not need to be performed. Besides, the case of changing the presence or absence or the sequence of the correction of physical characteristics as appropriate is also included in the invention.

Generally, in a successive approximation method that is based on objective function maximization, an objective function F expressed by the following formula (1) is maximized. Furthermore, in actual calculation, an algorithm for a gradient method for finding the minimum of a function only from the gradient (first-order differential) of the function (also called "gradient descent") or an optimization algorithm such as a Newton's method is used. Moreover, to avoid falling into a local solution, a combinatorial optimization, such as a genetic algorithm or an annealing method, can be incorporated.

$$F(\mu, y) = D(\mu, y) + \beta R(\mu) \quad (1)$$

Here, in the above formula (1), μ is a reconstructed image vector, and y is projection data. D, which is called a "data term", represents a degree of conformance with actual measured data, and is defined by, for example, a likelihood calculated from actual measured projection (actual measured projection data obtained by the X-ray detector 22) and an estimated parameter (an estimated image obtained by estimation in the above formula (1)). Furthermore, it should be noted that μ and y are vectors and are, therefore, actually spelled in bold.

R, which is generally called a "penalty term", reflects the validity of the estimated parameter (estimated image). In the present specification, hereinafter, R is referred to as a "validity term" for convenience sake. Substance information (substance constraint values m[1], . . . , m[N]), which is used in the invention and is described in detail in step S2 and subsequent steps, is reflected in the validity term. Furthermore, β is a coefficient used to control the intensity of the validity term R.

Specific examples of the validity term include a piecewise Gaussian function such as that illustrated in FIG. 3. In this case, a validity term is formed by connecting Gaussian distributions the respective centers of which are a plurality of estimated substance constraint values m[1], . . . , m[N]. The closer to the center of a Gaussian distribution the estimated pixel value is, the larger the objective function becomes, so that an action in which the estimated pixel value takes a value close to a substance constraint value works.

Furthermore, since the mean and dispersion of each distribution become parameters, the number of parameters to be given becomes "(the number of substances)×2", but only the mean value is updated for every iteration. In other words, "Update of Substance constraint Value" in step S6 described below means referring to the histogram of a reconstructed image for every iteration and correcting (shifting) the center position of each Gaussian distribution to an appropriate position.

The height and width (dispersion) of each Gaussian distribution are set based on an empirical rule. Moreover, the height and width (dispersion) of each Gaussian distribution can be individually set, or can be set by changing a switching position between mutually adjacent Gaussian distributions as appropriate. This step S1 is equivalent to an image update process in the invention.

(Step S2) Histogram Generation

A histogram is generated from the reconstructed image (estimated image) updated in step S1. Specifically, as illustrated in FIG. 4, a histogram in which the vertical axis is normalized with the maximum number of pixels and the horizontal axis represents pixel values divided with bin widths w is generated. As mentioned above, the horizontal axis of the histogram indicates a pixel value, which becomes higher as it comes closer to the right.

(Step S3) Peak Detection

An external value is detected as a peak from the histogram generated in step S2. Specifically, as illustrated in FIG. 4, when the height of the k-th bin in the histogram is denoted by h[k], all of the peaks satisfying "h[k−1]<h[k]>h[k+1]" are deemed as external values (in FIG. 4, illustrated with "●").

(Step S4) Peak Evaluation

Next, evaluation values each representing the likelihood of being a constituent substance are calculated with respect to all of the peaks detected in step S3. Specifically, as illustrated in FIG. 4, an evaluation value e[k] is assigned to the height h[k] (also called a "histogram value" or "peak value") of the k-th bin detected as a peak. It is considered that the larger the evaluation value e[k] is, the more probably the peak represents a constituent substance of the imaging sample. For example, a method of directly treating a histogram value h[k], detected as a peak, as the evaluation value e[k] can be considered.

Besides, for example, in a case where part of constituent substances of the imaging sample are known, a substance constraint value of the known substance is set as a reference substance constraint value. Alternatively, in a case where, as mentioned in (c), a substance constraint value is given as a parameter, the substance constraint value is set as a reference substance constraint value. As illustrated in FIG. 5, when the distance between a pixel value targeted for the evaluation value e[k] and the reference substance constraint value (in FIG. 5, expressed as "Distance from Reference Substance Constraint Value") is denoted by d (however, d not being negative), a method of defining the evaluation value e[k] based on the distance d from the reference substance constraint value and the histogram value h[k] can also be considered.

This is based on an idea that a substance constraint value to be estimated takes a value close to a known substance constraint value or a substance constraint value given as a parameter. In other words, it is considered that the evaluation value e[k] becomes smaller with distance from the reference substance constraint value (see FIG. 5). Therefore, an intensity coefficient concerning the evaluation value e is denoted by $e^{-\alpha d}$ ($\alpha$ being a constant) with use of the base (Napier's constant) e for natural logarithms and the distance d from the reference substance constraint value. This causes the distance d from the reference substance constraint value to become larger (longer) with distance from a pixel value corresponding to the reference substance constraint value, so that the intensity coefficient and, moreover, the evaluation value e[k] are defined to be small.

Furthermore, the reference substance constraint value does not need to be invariable. The substance constraint value given as a parameter or the known substance constraint value can be targeted for updating.

In the above-described way, the evaluation value e[k] is expressed by the following formula (2).

$$e[k]=h[k] \times e^{-\alpha d} \quad (2)$$

As mentioned above, the histogram value h[k] detected as a peak can be directly treated as the evaluation value e[k], or the evaluation value e[k] can be defined based on the distance d from the reference substance constraint value and the histogram value h[k] as in the above formula (2).

(Step S5) Peak Selection

Next, a peak that seems to correspond to a constituent substance is selected based on the evaluation value e[k] given in step S4 and a parameter that would be given if necessary. For example, assuming that the imaging sample is configured with N types of substances, N peaks are extracted in descending order of evaluation value, and these are treated as the peaks that have been detected (selected peaks). In a case where the number of constituent substances is unknown (for example, the case of granite stone or natural mineral (native mineral) or the case of an alloy that is an incomplete mixture of metals), peaks corresponding to evaluation values equal to or larger than a given evaluation value are treated as the selected peaks.

Besides, in a case where, regardless of the actual number of (for example, N) substance configuring the imaging sample, the number of constituent substances is designated as a parameter (a number different from N), peaks can be extracted in descending order of evaluation value based on the parameter and these can be treated as the selected peaks. Furthermore, to which substance the peak that has been selected corresponds does not need to be recognized in advance. Moreover, a peak that has not been selected is discarded at this point.

This means that peaks indicating N pieces of substance information (peak numbers: $k_1, \ldots, k_N$) have been selected as illustrated in FIG. 4. Since the selected peak numbers $k_1, \ldots, k_N$ are not consecutive numbers, the selected peak numbers are permuted as $k_1=1, \ldots, k_N=N$ in such a way as to become consecutive numbers as $1, \ldots, N$. Then, when the pixel value corresponding to the n-th bin of the histogram is denoted by $v[k_n]=w \times (k_n-0.5)$, the substance constraint value, which is a specific value of the substance information, is calculated as $v[k_1]=m[1], \ldots, v[k_N]=m[N]$.

While, in the above formula ($v[k_n]=w \times (k_n-0.5)$), 0.5 is subtracted from the peak number $k_n$ so as to perform shifting from the peak number $k_n$ to the center of the bin width w, the formula used to calculate a substance constraint value is not limited to the above formula. The substance constraint value can be calculated by a linear function with the peak number $k_n$ set as a variable.

(Step S6) Update of Substance Constraint Value

According to the above processing, $m[1], \ldots, m[N]$, which are N pieces of substance information (a substance constraint value=a pixel value representing an X-ray absorption coefficient of each substance), have been estimated and updated. In other words, a pixel value corresponding to the peak selected in step S5 (selected peak) is set as a substance constraint value to be used for successive approximation calculation in step S1 performed in returning to next step S1. In the above-described way, steps S2 to S6 are equivalent to a substance information estimation process in the invention.

(Step S7) Increment of Counter Variable of Iteration Count

A counter variable of the repeat count (iteration count) in successive approximation formulae is incremented.

(Step S8) End of Image Update?

When an iteration count at which to end image update performed by the successive approximation method is denoted by $N_{iter}$, it is determined whether the counter variable has reached the iteration count $N_{iter}$. Furthermore, the iteration count $N_{iter}$ can be previously set by the operator. If the counter variable is equal to or less than $N_{iter}$, the processing returns to step S1 to continue steps S1 to S6. If the counter variable has exceeded $N_{iter}$, the processing ends a series of calculations.

The estimated image obtained in this way is acquired as a reconstructed image. Moreover, without setting the iteration count $N_{iter}$, the operator can observe an estimated image obtained at every update, the operator can interrupt a series of calculations based on a result of the observation, and the estimated image obtained at that time can be acquired as a reconstructed image. Alternatively, the determination can be made according to whether some kind of convergence evaluation value (for example, a value of the objective function) has exceeded or has fallen below a determination criterion value.

According to the image reconstruction processing method related to the present embodiment, in the substance information estimation process (in FIG. 2, steps S2 to S6), substance information (in the present embodiment, substance constraint values $m[1], \ldots, m[N]$) is estimated from a reconstructed image for every image update in the image update process (in FIG. 2, step S1), and images are updated in succeeding calculations by successive approximation formulae in the successive approximation method using the substance information (substance constraint values $m[1], \ldots, m[N]$) estimated in the substance information estimation process (steps S2 to S6). In this way, estimating substance information (substance constraint values $m[1], \ldots, m[N]$) from a reconstructed image enables the invention to be applied regardless of whether constituent substances of an imaging sample are known or unknown.

Moreover, as also mentioned in the section of "Means for Solving the Problems", while, in Patent Literature 1: U.S. Pat. No. 8,175,361, the estimated substance information is fixed, in the present embodiment, substance information (substance constraint values $m[1], \ldots, m[N]$) is estimated (updated) from a reconstructed image for every image update in the image update process (step S1), so that reliable substance information (substance constraint values $m[1], \ldots, m[N]$) can be estimated while avoiding such a problem that, for example, the substance information estimated at a point of time when a repeat count (iteration count) by successive approximation formulae is low is continuously used even at a point of time when the repeat count is high. Accordingly, artifacts can be reduced using the reliable substance information (substance constraint values m[1], ..., m[N]).

Moreover, (a) substance information, which is to be estimated, can be estimated based on the number of known constituent substances, (b) substance information, which is to be estimated, can be estimated based on the number of constituent substances given as a parameter, or (c) substance information, which is to be estimated, can be estimated based on a substance constraint value given as a parameter. In the case of (a) mentioned above, for example, N peaks are extracted in descending order of evaluation value, as also mentioned in step S5, based on the number (for example, N) of known constituent substances, and these peaks are treated as selected peaks to estimate substance information (substance constraint values m[1], ..., m[N]).

Moreover, in the case of (b) mentioned above, in a case where, regardless of the actual number (for example, N) of substances configuring the imaging sample, the number (a number different from N) of constituent substances is designated as a parameter, substance information is estimated based on this parameter. For example, as also mentioned in step S5, a number different from N, which is the actual number of substances, is designated as a parameter, peaks are extracted in descending order of evaluation value based on this parameter, and these peaks are treated as selected peaks to estimate substance constraint values.

Moreover, in the case of (c) mentioned above, in a case where, regardless of whether constituent substances are known or unknown, a substance constraint value is given as a parameter, substance information is estimated based on this parameter. For example, as also mentioned in step S4, in a case where a substance constraint value is given as a parameter, the substance constraint value is treated as a reference substance constraint value. Then, an evaluation value e[k] is calculated based on the reference substance constraint value, and, as also mentioned in step S5, peaks are selected based on the evaluation value e[k] to estimate substance constraint values.

According to (a) mentioned above to (c) mentioned above, the possibility of erroneous substance information being estimated can be reduced or prevented. As also mentioned in the section of "Means for Solving the Problems", substance information can be estimated by any one of (a) mentioned above to (c) mentioned above, or the substance information can be estimated by a combination of some of (a) mentioned above to (c) mentioned above. For example, the substance information can be estimated by a combination of (a) mentioned above and (c) mentioned above, or the substance information can be estimated by a combination of (b) mentioned above and (c) mentioned above.

In the present embodiment, as illustrated in the flowchart of FIG. 2, substance information to be estimated (substance constraint values m[1], ..., m[N]) is estimated based on the histogram of a reconstructed image generated in step S2.

According to the image reconstruction processing program 8A (see FIG. 1) related to the present embodiment, a computer (in the present embodiment, a CPU or GPU configuring the reconstruction processing unit 7 illustrated in FIG. 1) is caused to perform the image reconstruction processing method (see the flowchart of FIG. 2) related to the present embodiment, so that the invention can be applied regardless of whether constituent substances of an imaging sample are known or unknown, reliable substance information (substance constraint values m[1], ..., m[N]) can be estimated, and artifacts can be reduced using the reliable substance information.

According to the tomography device (in the present embodiment, an X-ray CT device) related to the present embodiment, calculation means (in the present embodiment, a CPU or GPU configuring the reconstruction processing unit 7 illustrated in FIG. 1) for executing the image reconstruction processing program 8A is included, so that the invention can be applied regardless of whether constituent substances of an imaging sample are known or unknown, reliable substance information (substance constraint values m[1], ..., m[N]) can be estimated, and artifacts can be reduced using the reliable substance information.

[Reconstruction Result]

A reconstruction result is described with reference to FIG. 6 to FIG. 8. FIG. 6 illustrates a reconstruction result obtained when no substance information is present, FIG. 7 illustrates a reconstruction result obtained when substance information is not updated, and FIG. 8 illustrates a reconstruction result obtained when substance information has been updated. In FIG. 6 and FIG. 7, artifacts in the shape of diagonal streaks (streak artifacts) are observed. In contrast to those, in a case where substance information has been updated as in the invention, in FIG. 8, it is observed that artifacts disappear and the image quality has been improved.

The invention is not limited to the above-described embodiment, but can be implemented in modified manners as described below.

(1) While, in the above-described embodiment, the tomography device is described with an X-ray CT device taken as an example, the tomography device is not specifically limited as long as it performs reconstruction processing by a successive approximation method. The embodiment can also be applied to, for example, a magnetic resonance imaging (MRI) device, an optical CT device, and a tomography device using radiation other than X-rays (for example, α radiation, β radiation, or γ radiation).

(2) The above-described embodiment is applied to an inspection device for manufacturing use or industrial use such as that illustrated in FIG. 1, but can also be applied to a medical device with human bodies or small animals targeted as a subject.

(3) As, for example, single-wavelength X-rays (monochromatic X-rays) or X-rays having a plurality of wavelengths (polychromatic X-rays) can be taken as an example, the type of X-rays to be applied is not specifically limited.

(4) While the above-described embodiment has an imaging configuration illustrated in FIG. 1, as, for example, tomosynthesis can be taken as an example, the imaging configuration concerning tomography is not specifically limited.

(5) While, in the above-described embodiment, substance information (in the embodiment, substance constraint values m[1], ..., m[N]) is estimated from a reconstructed image for every image update in the image update process (in FIG. 2, step S1), substance information (substance constraint values m[1], ..., m[N]) can be estimated from a reconstructed image at given intervals, at timing satisfying a given standard, or at optional timing.

(6) The histogram in the above-described embodiment is not limited to the one generated from all of the pixels of a reconstructed image, but can be generated from an optional set of pixels or an image subjected to some image processing, such as down sampling processing which is conversion processing for lowering the sampling frequency.

(7) With regard to peak detection (see step S3 in the flowchart of FIG. 2) in the above-described embodiment, peaks can be detected in consideration of the area of the periphery of an external value.

(8) While, in the above-described embodiment, as illustrated in the flowchart of FIG. 2, substance information to be estimated (in the embodiment, substance constraint values m[1], . . . , m[N]) is estimated based on the histogram of a reconstructed image generated in step S2, substance information to be estimated (substance constraint values m[1], . . . , m[N]) can be estimated based on a result of clustering of a reconstructed image, as illustrated in the flowchart of FIG. 9. Specifically, clustering processing, such as a k-means method (also called "k-means clustering") for partitioning into k given clusters using the mean of clusters, is applied to a reconstructed image (step T2), a cluster center of mass calculated in step T3 is selected (step T4), and a pixel value at the position of the selected cluster center of mass is treated as a substance constraint value (step T5). Performing the flowchart of FIG. 9 enables bringing about an advantageous effect similar to that in the flowchart of FIG. 2 described in the embodiment. It should be noted that k as used herein differs in meaning from k representing a bin number in the histogram described in the embodiment.

As described above, for example, the invention is suitable for an inspection device or a medical device for manufacturing use or industrial use, such as an X-ray CT device (for example, a tomosynthesic device), an MRI device, or an optical CT device.

The invention claimed is:

1. An image reconstruction processing method that performs reconstruction processing, the image reconstruction processing method comprising:

updating a histogram of an image by a successive approximation method in a histogram update process; and estimating substance information from a reconstructed image for every histogram update in the histogram update process, at given intervals, at timing satisfying a given standard, or at optional timing, in a substance information estimation process, wherein the histogram reconstruction processing method performs reconstruction processing while updating the image by the successive approximation method in the image update process using the substance information estimated in the substance information estimation process.

2. The image reconstruction processing method according to claim 1, further comprising:

(a) estimating the substance information, which is to be estimated, based on a number of known constituent substances.

3. The image reconstruction processing method according to claim 2, further comprising:

(b) estimating the substance information, which is to be estimated, based on a number of constituent substances given as a parameter.

4. The image reconstruction processing method according to claim 3, further comprising:

(c) estimating the substance information, which is to be estimated, based on a substance constraint value given as a parameter.

5. The image reconstruction processing method according to claim 1, further comprising:

estimating the substance information, which is to be estimated, based on a histogram of the reconstructed image or a result of clustering of the reconstructed image.

6. A non-transitory computer readable medium storing an image reconstruction processing program characterized by causing a computer to perform the image reconstruction processing method according to claim 1.

7. A tomography device equipped with the image reconstruction processing program according to claim 6, the tomography device further comprising:

at least one processor for executing the image reconstruction processing program.

8. The image reconstruction processing method according to claim 1, further comprising:

the substance information functions for updating the histogram so that the pixel value distribution with a width become close to precipitous peak.

* * * * *